US006626873B1

(12) United States Patent
Modak et al.

(10) Patent No.: US 6,626,873 B1
(45) Date of Patent: *Sep. 30, 2003

(54) TRICOLOSAN-CONTAINING MEDICAL DEVICES

(75) Inventors: Shanta Modak, River Edge, NJ (US); Lester Sampath, Nyack, NJ (US)

(73) Assignee: Trustees of Columbia University, New York, NY (US)

( * ) Notice: Subject to any disclaimer, the term of this patent is extended or adjusted under 35 U.S.C. 154(b) by 216 days.

This patent is subject to a terminal disclaimer.

(21) Appl. No.: 09/618,432

(22) Filed: Jul. 18, 2000

Related U.S. Application Data

(63) Continuation of application No. 09/101,129, filed as application No. PCT/US96/20932 on Dec. 23, 1996, now Pat. No. 6,106,505, which is a continuation-in-part of application No. 08/583,239, filed on Jan. 5, 1996, now Pat. No. 5,772,640.

(51) Int. Cl.$^7$ .............................................. A61M 5/32
(52) U.S. Cl. ........................ 604/265; 424/422; 623/1.1; 428/35.1
(58) Field of Search .................... 604/264, 265; 428/35.7, 36.9; 606/76; 424/422; 623/1.1, 1.42, 1.43, 1.45

(56) References Cited

U.S. PATENT DOCUMENTS

| | | |
|---|---|---|
| 4,605,564 A | 8/1986 | Kulla et al. |
| 4,723,950 A | 2/1988 | Lee |
| 4,994,047 A | 2/1991 | Walker et al. |
| 4,999,210 A | 3/1991 | Solomon et al. ............... 427/2 |
| 5,013,306 A | 5/1991 | Solomon et al. ............ 604/265 |
| 5,019,096 A | 5/1991 | Fox, Jr. et al. |
| 5,033,488 A | 7/1991 | Curtis et al. |
| 5,089,205 A | 2/1992 | Huang et al. ............... 264/255 |
| 5,091,442 A | 2/1992 | Milner |
| 5,102,401 A | 4/1992 | Lambert et al. |
| 5,165,952 A | 11/1992 | Solomon et al. |
| 5,180,605 A | 1/1993 | Milner |
| 5,200,194 A | 4/1993 | Edgren et al. |
| 5,209,251 A | 5/1993 | Curtis et al. |
| 5,261,421 A | 11/1993 | Milner |
| 5,335,373 A | 8/1994 | Dangman et al. |
| 5,357,636 A | 10/1994 | Dresdner, Jr. et al. |
| 5,451,424 A | 9/1995 | Solomon et al. ............. 427/2.1 |
| 5,707,366 A | 1/1998 | Solomon et al. ............ 604/265 |
| 6,261,271 B1 | 7/2001 | Solomon et al. ............ 604/265 |

FOREIGN PATENT DOCUMENTS

| | | |
|---|---|---|
| WO | 9302717 | 2/1993 |
| WO | 9306881 | 4/1993 |
| WO | 9622114 | 7/1996 |

OTHER PUBLICATIONS

Bach et al., 1994, "Prevention of bacterial colonization of intravenous catheters by antiseptic impregnation of polyurethane polymers," Journal of Antimicrobial Chemotherapy, 33:969–978.

Primary Examiner—Sharon Kennedy
(74) Attorney, Agent, or Firm—Baker Botts L.L.P.

(57) ABSTRACT

The present invention relates to polymeric medical articles comprising the anti-infective agents chlorhexidine and triclosan. It is based, at least in part, on the discovery that the synergistic relationship between these compounds permits the use of relatively low levels of both agents, and on the discovery that effective antimicrobial activity may be achieved when these compounds are comprised in either hydrophilic or hydrophobic polymers. It is also based on the discovery that chlorhexidine free base and triclosan, used together, are incorporated into polymeric medical articles more efficiently. Medical articles prepared according to the invention offer the advantage of preventing or inhibiting infection while avoiding undesirably high release of anti-infective agent, for example into the bloodstream of a subject.

30 Claims, No Drawings

TRICOLOSAN-CONTAINING MEDICAL DEVICES

This application is a continuation of U.S. patent application Ser. No. 09/104,129, U.S. Pat. No. 6,105,505, filed Jun. 30, 1998, which is a national phase application pursuant to 35 U.S.C. §371 of PCT/US96/20932, filed Dec. 23, 1996, which is a continuation-in-part of U.S. patent application Ser. No. 08/583,239, filed Jan. 5, 1996, now issued as U.S. Pat. No. 5,772,640.

BACKGROUND OF THE INVENTION

The present invention relates to medical devices comprising synergistic combinations of triclosan and chlorhexidine.

Whenever a medical device comes in contact with a patient, a risk of infection is created. Thus, a contaminated examination glove, tongue depressor, or stethoscope could transmit infection. The risk of infection dramatically increases for invasive medical devices, such as intravenous catheters, arterial grafts, intrathecal or intracerebral shunts and prosthetic devices, which not only are, themselves, in intimate contact with body tissues and fluids, but also create a portal of entry for pathogens.

A number of methods for reducing the risk of infection have been developed which incorporate anti-infective agents into medical devices, none of which have been clinically proven to be completely satisfactory. Such devices desirably provide effective levels of anti-infective agent during the entire period that the device is being used. This sustained release may be problematic to achieve, in that a mechanism for dispersing anti-infective agent over a prolonged period of time may be required, and the incorporation of sufficient amounts of anti-infective agent may adversely affect the surface characteristics of the device. The difficulties encountered in providing effective anti-microbial protection increase with the development of drug-resistant pathogens.

One potential solution to these problems is the use of a synergistic combination of anti-infective agents that requires relatively low concentrations of individual anti-infective agents which may have differing patterns of bioavailability.

Two well known anti-infective agents are chlorhexidine and triclosan. The following patents and patent application relate to the use of chlorhexidine and/or triclosan in medical devices.

U.S. Pat. No. 4,723,950 by Lee relates to a microbicidal tube which may be incorporated into the outlet tube of a urine drainage bag. The microbicidal tube is manufactured from polymeric materials capable of absorbing and releasing anti-microbial substances in a controllable, sustained, time-release mechanism, activated upon contact with droplets of urine, thereby preventing the retrograde migration of infectious organisms into the drainage bag. The microbicidal tube may be produced by one of three processes: (1) a porous material, such as polypropylene, is impregnated with at least one microbicidal agent, and then coated with a hydrophilic polymer which swells upon contact with urine, causing the leaching-out of the microbicidal agent; (2) a porous material, such as high density polyethylene, is impregnated with a hydrophilic polymer and at least one microbicidal agent; and (3) a polymer, such as silicone, is compounded and co-extruded with at least one microbicidal agent, and then coated with a hydrophilic polymer. A broad range of microbicidal agents are disclosed, including chlorhexidine and triclosan, and combinations thereof. The purpose of Lee's device is to allow the leaching out of microbicidal agents into urine contained in the drainage bag; similar leaching of microbicidal agents into the bloodstream of a patient may be undesirable.

U.S. Pat. No. 5,091,442 by Milner relates to tubular articles, such as condoms and catheters, which are rendered antimicrobially effective by the incorporation of a non-ionic sparingly soluble antimicrobial agent, such as triclosan. The tubular articles are made of materials which include natural rubber, polyvinyl chloride and polyurethane. Antimicrobial agent may be distributed throughout the article, or in a coating thereon. A condom prepared from natural rubber latex containing 1% by weight of triclosan, then dipped in an aqueous solution of chlorhexidine, is disclosed. U.S. Pat. Nos. 5,180,605 and 5,261,421, both by Milner, relate to similar technology applied to gloves.

U.S. Pat. Nos. 5,033,488 and 5,209,251, both by Curtis et al., relate to dental floss prepared from expanded polytetrafluoroethylene (PTFE) and coated with microcrystalline wax. Antimicrobial agents such as chlorhexidine or triclosan may be incorporated into the coated floss.

U.S. Pat. No. 5,200,194 by Edgren et al. relates to an oral osmotic device comprising a thin semipermeable membrane wall surrounding a compartment housing a "beneficial agent" (that is at least somewhat soluble in saliva) and a fibrous support material composed of hydrophilic water-insoluble fibers. The patent lists a wide variety of "beneficial agents" which may be incorporated into the oral osmotic device, including chlorhexidine and triclosan.

U.S. Pat. No. 5,019,096 by Fox, Jr. et al. relates to infection-resistant medical devices comprising a synergistic combination of a silver salt (such as silver sulfadiazine) and chlorhexidine.

International Patent Application No. PCT/GB92/01481, Publication No. WO 93/02717, relates to an adhesive product comprising residues of a co-polymerizable emulsifier comprising a medicament, which may be povidone iodine, triclosan, or chlorhexidine.

In contrast to the present invention, none of the above-cited references teach medical articles comprising synergistic combinations of chlorhexidine and triclosan which utilize relatively low levels of these agents.

SUMMARY OF THE INVENTION

The present invention relates to polymeric medical articles comprising the anti-infective agents chlorhexidine and triclosan. It is based, at least in part, on the discovery that the synergistic relationship between these compounds permits the use of relatively low levels of both agents, and on the discovery that effective antimicrobial activity may be achieved when these compounds are comprised in either hydrophilic or hydrophobic polymers. It is also based on the discovery that chlorhexidine free base and triclosan, used together, are incorporated into polymeric medical articles more efficiently. Medical articles prepared according to the invention offer the advantage of preventing or inhibiting infection while avoiding undesirably high release of anti-infective agent, for example into the bloodstream of a subject.

DETAILED DESCRIPTION OF THE INVENTION

The present invention relates to medical articles comprising synergistic combinations of chlorhexidine and triclosan.

Chlorhexidine may be provided by way of any form, salt or derivative thereof, including but not limited to chlorhexidine free base and chlorhexidine salts such as chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-α-hydroxyisobutyrate, chlorhexidine diglucoheptonate, chlorhexidine di-isothionate, chlorhexidine dibenzoate, chlorhexidine dicinnarnate, chlorhexidine dimandelate, chlorhexidine di-isophthalate, chlorhexidine di-2-hydroxynaphthoate, and chlorhexidine embonate. The term "chlorhexidine", as used herein, may refer to any of such forms, derivatives, or salts, unless specified otherwise. Chlorhexidine salts may be solubilized using polyethylene glycol or propylene glycol, or other solvents known in the art.

The term triclosan refers to a compound also known as 2,4,4'-trichloro-2'-hydroxydiphenyl ether.

Medical articles that may be treated according to the invention are either fabricated from or coated or treated with biomedical polymer and include, but are not limited to, catheters including urinary catheters and vascular catheters (e.g., peripheral and central vascular catheters), wound drainage tubes, arterial grafts, soft tissue patches, gloves, shunts, stents, tracheal catheters, wound dressings, sutures, guide wires and prosthetic devices (e.g., heart valves and LVADs). Vascular catheters which may be prepared according to the present invention include, but are not limited to, single and multiple lumen central venous catheters, peripherally inserted central venous catheters, emergency infusion catheters, percutaneous sheath introducer systems and thermodilution catheters, including the hubs and ports of such vascular catheters.

The present invention may be further applied to medical articles that have been prepared according to U.S. Pat. No. 5,019,096 by Fox, Jr. et al.

The present invention provides, in various alternative non-limiting embodiments, for: (1) compositions which provide a local concentration of chlorhexidine of between 100 and 2000 μg/ml and a local concentration of triclosan of between 250 and 2000 μg/ml; (2) treatment solutions of a polymer comprising between 1 and 5 percent, and preferably between 1.5 and 2.25 percent, of chlorhexidine; and between 0.5 and 5 percent, and preferably between 0.5 and 2 percent, of triclosan, wherein a medical article may be dipped or soaked in the polymer solution; (3) medical articles treated with a treatment solution as set forth in (2) above, and articles physically equivalent thereto (that is to say, articles prepared by a different method but having essentially the same elements in the same proportions); (4) treatment solutions of a polymer comprising between 1 and 5 percent, and preferably between 1.5 and 2.25 percent, of chlorhexidine; between 0.5 and 5 percent, and preferably between 0.5 and 2 percent, of triclosan; and between 0.5 and 1 percent (preferably 0.75 percent) of silver sulfadiazine, wherein a medical article may be dipped or soaked in the polymer solution; and (5) medical articles treated with a treatment solution set forth in (4) above, and articles physically equivalent thereto (that is to say, articles prepared by a different method but having essentially the same elements in the same proportions). Percentages recited herein refer to percent by weight, except as indicated otherwise.

In preferred embodiments, the ratio, by weight, of the total amount of anti-infective agent to polymer in the treatment solution is less than 1.5.

In one particular non-limiting embodiment, the present invention provides for a hydrophilic polymeric medical article (i.e., a medical article fabricated from a hydrophilic polymer) treated by dipping or soaking the article in a treatment solution of a hydrophilic polymer comprising chlorhexidine and triclosan wherein the chlorhexidine and triclosan are present in amounts such that their combination, in the treated article, has effective antimicrobial activity. The terms "treat", "treated", etc., as used herein, refer to coating, impregnating, or coating and impregnating a medical article with polymer/anti-infective agent. The term "hydrophilic polymer", as used herein, refers to polymers which have a water absorption greater than 0.6 percent by weight (and, in preferred embodiments, less than 2 percent by weight; as measured by a 24 hour immersion in distilled water, as described in ASTM Designation D570-81) including, but not limited to biomedical polyurethanes (e.g., ether-based polyurethanes and ester-based polyurethanes, as set forth in Baker, 1987, in *Controlled Release of Biologically Active Agents*, John Wiley and Sons, pp. 175–177 and Lelah and Cooper, 1986, *Polyurethanes in Medicine*, CRC Press, Inc., Florida pp. 57–67; polyurethanes comprising substantially aliphatic backbones such as Tecoflex™ 93A; polyurethanes comprising substantially aromatic backbones such as Tecothane™; and Pellethane™), polylactic acid, polyglycolic acid, natural rubber latex, and gauze or water-absorbent fabric, including cotton gauze and silk suture material. In a specific, non-limiting embodiment, the hydrophilic medical article is a polyurethane catheter which has been treated with (i.e., dipped or soaked in) a treatment solution comprising (i) between about 1 and 10 percent, preferably between about 2 and 6 percent, and more preferably about 3 percent, of a biomedical polyurethane; (ii) between 1 and 5 percent, and preferably between 1.5 and 2.25 percent, of chlorhexidine; and (iii) between 0.5 and 5 percent, and preferably between 0.5 and 2 percent, of triclosan. In related non-limiting embodiments of the invention, the treatment solution may further comprise silver sulfadiazine, preferably in a concentration of between 0.5 and 1 percent (more preferably 0.75 percent). Section 6, below, presents working examples of embodiments set forth in this paragraph.

In another particular non-limiting embodiment, the present invention provides for a hydrophilic polymeric medical article treated by dipping or soaking the article in a treatment solution of a hydrophobic polymer comprising chlorhexidine and triclosan, wherein the chlorhexidine and triclosan are present in amounts such that their combination, in the treated article, has effective antimicrobial activity. The term "hydro-phobic polymer", as used herein, refers to a polymer which has a water absorption of less than 0.6 percent and includes, but is not limited to, silicone polymers such as biomedical silicones (e.g., Silastic Type A) or elastomers (e.g., as set forth in Baker, 1987, in *Controlled Release of Biologically Active Agents*, John Wiley and Sons, pp.156–162), Dacron, polytetrafluoroethylene (PTFE, also "Teflon"), polyvinyl chloride, cellulose acetate, polycarbonate, and copolymers such as silicone-polyurethane copolymers (e.g., PTUE 203 and PTUE 205 polyurethane-silicone interpenetrating polymer). In a specific, non-limiting embodiment, the medical article is a polyurethane catheter which has been dipped or soaked in a treatment solution comprising (i) between about 1 and 10 percent, preferably between about 2 and 6 percent, and more preferably about 3 percent, of a polyurethane-silicone copolymer; (ii) between 1 and 5 percent, and preferably between 1.5 and 2.25 percent, of chlorhexidine; and (iii) between 0.5 and 5 percent, and preferably between 0.5 and 2 percent, of triclosan. In related non-limiting embodiments of the invention, the treatment solution may further comprise silver sulfadiazine, preferably in a concentration of between 0.5 and 1 percent (more preferably 0.75 percent). Section 7, below, presents working examples of embodiments set forth in this paragraph.

In another particular non-limiting embodiment, the present invention provides for a hydrophobic polymeric medical article treated by dipping or soaking the article in a treatment solution of hydrophobic polymer comprising chlorhexidine and triclosan, wherein the chlorhexidine and triclosan are present in amounts such that their combination, in the treated article, has effective antimicrobial activity. In a specific, non-limiting embodiment, the medical article is a silicone catheter or a polyvinylchloride catheter which has been dipped or soaked in a treatment solution comprising (i) between about 1 and 10 percent, and preferably about 5 percent, of a silicone polymer; (ii) between 1 and 5 percent, and preferably between 1.5 and 2.25 percent, of chlorhexidine; and (iii) between 0.5 and 5 percent, and preferably between 0.5 and 2 percent, of triclosan. In related non-limiting embodiments of the invention, the treatment solution may further comprise silver sulfadiazine, preferably in a concentration of between 0.5 and 1 percent (more preferably 0.75 percent). In still other related embodiments, a coating of a hydrophobic polymer may be applied over the treated article. Section 8, below, presents working examples of embodiments set forth in this paragraph.

In another particular non-limiting embodiment, the present invention provides for a hydrophobic polymeric medical article treated by dipping or soaking the article in a treatment solution of hydrophilic polymer comprising chlorhexidine and triclosan, wherein the chlorhexidine and triclosan are present in amounts such that their combination, in the treated article, has effective antimicrobial activity. In a specific, non-limiting embodiment, the medical article is a silicone catheter or Teflon graft which has been dipped or soaked in a treatment solution comprising (i) between about 1 and 10 percent, preferably between about 2 and 6 percent, and more preferably about 3 percent, of a biomedical polyurethane polymer; (ii) between 1 and 5 percent, and preferably between 1.5 and 2.25 percent, of chlorhexidine; and (iii) between 0.5 and 5 percent, and preferably between 0.5 and 2 percent, of triclosan. In related non-limiting embodiments of the invention, the treatment solution may further comprise silver sulfadiazine, preferably in a concentration of between 0.5 and 1 percent (more preferably 0.75 percent).

Medical articles prepared according to the invention may be treated on their external surface, internal surface, or both. For example, and not by way of limitation, where the medical article is a catheter, the internal surface and/or external surface of the catheter may be treated according to the invention. For example, where it is desired to treat both internal and external surfaces, an open-ended catheter may be placed in a treatment solution such that the treatment solution fills the catheter lumen. If only the external surface is to come in contact with treatment solution, the ends of the catheter may be sealed before it is placed in the treatment solution. If only the internal surface is to come in contact with treatment solution, the solution may be allowed to pass through and fill the lumen but the catheter is not immersed in the treatment solution.

Successful treatment of a medical article with a polymer comprising an anti-infective agent may be problematic, particularly where the medical article has a hydrophobic surface. The adherence of the polymer may depend upon (1) the polymeric matrix in which the anti-infective agent is suspended; (2) compatibility (or lack thereof) between the agent-polymeric matrix and the surface of the article; (3) the solvent system; and (4) the thickness of polymer/anti-infective agent desirably applied. Furthermore, the rates of release of various anti-infective agents from diverse polymers may differ. For example, the rate of release of chlorhexidine from a silicone matrix is faster than the rate of release of silver sulfadiazine from the same matrix. In order to compensate for this difference, one potential solution would be to increase the amounts of chlorhexidine and silver sulfadiazine in the matrix. Unfortunately, polymers comprising high levels of chlorhexidine and silver sulfadiazine have been found to adhere poorly to silicone catheters. In order to provide an alternative solution to the problem, two different methods for treating medical articles have been developed: a one-step method, and a two-step method, both of which are set forth below.

According to the one-step method of the invention, a polymeric medical article may be treated with a solution comprising one or more anti-infective agents, and optionally containing a biomedical polymer, dissolved in one or more solvent(s), wherein the solvent(s) selected are capable of swelling the polymeric medical article to be treated; such a solution is referred to herein as an "impregnating solution", and the process by which the article is treated with anti-infective agent is referred to as "impregnation". Suitable solvents include, but are not limited to, tetrahydrofuran ("THF"), dichloromethane, carbon tetrachloride, methanol, ethanol, methyl ethyl ketone, heptane, and hexane, and mixtures thereof. The biomedical polymer may be hydrophilic or hydrophobic, and includes the various polymers set forth above.

If a hydrophilic polymeric medical article is to be impregnated with chlorhexidine and triclosan, the impregnating solution may, in specific non-limiting embodiments, comprise the following (percentages of solvents in this paragraph being volume/volume): (1) 95% ethanol; (2) 70% ethanol/30% water; (3) 50% ethanol/50% water; (4) 30% reagent alcohol/70% THF containing 2–3% of a biomedical polyurethane; (5) 90% reagent alcohol/10% THF; or (6) 100% reagent alcohol. Preferred soaking times vary between 5 minutes and 1 hour.

In specific, non-limiting embodiments of the invention, a hydrophilic medical article such as a polyurethane catheter may be impregnated using a solvent mixture of 70–90% ethanol and 10–30% water and chlorhexidine and triclosan for between 10 and 60 minutes. The article may then be dried for 24–48 hours.

If a hydrophobic polymeric medical article is to be impregnated with chlorhexidine and triclosan, the impregnating solution may, in specific non-limiting embodiments, comprise the following (percentages of solvents in this paragraph being volume/volume): (1) 10% methanol /90% THF; (2) 10% ethanol/90% THF; (3) 30% methanol/70% THF; (4) 30% ethanol/70% THF; (5) 1–5 percent silicone polymer in 10% methanol/90% THF; (6) 1–5 percent silicone polymer in 10% ethanol/90% THF; (7) 1–2 percent polylactic acid in 10% methanol/90% THF; (8) 1–2 percent polylactic acid in 10% ethanol/90% THF; (9) 1–5 percent silicone polymer in 30% methanol/70% THF; (10) 1–5 percent silicone polymer in 30% ethanol/70% THF; (11) 1–2 percent polylactic acid in 30% methanol/70% THF; (12) 1–2 percent polylactic acid in 30% ethanol/70% THF; (13) 1–5 percent silicone polymer in 100% methyl ethyl ketone; and (14) 1–2 percent polyurethane in 30% ethanol/70% THF. For specific examples, see Section 15, below.

In specific embodiments, the impregnating solution comprises between 0.2 and 10 percent anti-infective agent and between 0.5 and 4 percent biomedical polymer.

The medical article, or a portion thereof, may be immersed in the impregnating solution to swell, after which the article may be removed and dried at room temperature until all solvent has evaporated and the article is no longer swollen. During the swelling process, anti-infective agent (and small amounts of polymer when present in the impregnating solution) may be distributed within the polymeric substrate of the article; during drying, the anti-infective agent and biomedical polymer (where present) may migrate somewhat toward the surface of the article. After drying, the article may be rinsed in either water or alcohol and wiped to remove any excess anti-infective agent and/or polymer at the surface. This may leave a sufficient amount of anti-infective agent just below the surface of the article, thereby permitting sustained release of the agent over a prolonged period of time. Anti-infective agents which may be incorporated by this process include but are not limited to chlorhexidine, triclosan, silver sulfadiazine, parachlorometaxylene, benzalkonium chloride, bacitracin, polymyxin, miconasole and rifampicin, as well as combinations thereof.

In preferred, non-limiting embodiments of the invention, synergistic combinations of chlorhexidine and triclosan may be dissolved in a mixture of methanol and tetrahydrofuran to produce an impregnating solution that may be used to render a silicone catheter anti-infective.

In one specific, non-limiting example, the amount of chlorhexidine may be between 1 and 5 percent and preferably between 1.5 and 2.25 percent of the impregnating solution, and the amount of triclosan may be between 0.5 and 5 percent, and preferably between 0.5 and 2 percent. The resulting impregnating solution may further contain between 1 and 10 percent and preferably between 2 and 4 percent of a biomedical polymer such as a silicone polymer (e.g., Silastic Type A), polyurethane, or polycaprolactone. Specific examples of the one-step method are provided in Section 12 below.

According to the two-step method of the invention, the one-step method may be used to impregnate a medical article with anti-infective agent, and then the medical article may be dipped into a polymeric solution and dried. This method forms a polymeric coating on the article and further controls the rate of release of anti-infective agent. When the two-step method is practiced, the biomedical polymer may be omitted from the first soaking step. Optionally, an anti-infective agent may further be comprised in the polymeric coating. In a specific, non-limiting example, a silicone catheter may be dipped in a mixture of methanol and tetrahydrofuran containing between about 1 and 5 percent, and preferably between 1.5 and 2.25 percent, of chlorhexidine; between 0.5 and 5 percent and preferably between 0.5 and 2 percent of triclosan; and between 1 and 10 percent, and preferably between 2 and 4 percent, of a biomedical polymer (preferably a silicone polymer such as Silastic Type A) for about 30 minutes, dried, and then dipped in a higher concentration (but less than 10 percent) of biomedical polymer dissolved in a suitable solvent. For example, but not by way of limitation, a coating may be applied using a solution of 30% ethanol/70% THF containing 2–3 percent of a biomedical polyurethane, or a solution of 1–5 percent of Silastic Type A.

Alternatively, a hydrophilic medical article, such as a polyurethane catheter, may be impregnated with one or more antimicrobial agents and then coated with a polymer.

Examples of the two-step method are set forth in Sections 8, 16 and 17 below.

As set forth in Section 17, below, it has further been discovered that when medical articles were treated with mixtures of chlorhexidine free base and triclosan, uptake of chlorhexidine and triclosan was enhanced, and the antimicrobial activity of such articles was improved. While not desiring to be bound to any particular theory, it is believed that chlorhexidine free base and triclosan form a complex with improved solubility. The foregoing effect was observed when chlorhexidine free base and triclosan were combined in a respective molar ratio of 1:2; according to the invention, chlorhexidine free base and triclosan may be dissolved in a solvent or solvent system at chlorhexidine free base: triclosan molar ratios of 1:1 to 1:3. The total weight percent of chlorhexidine free base plus triclosan is between 1 and 10 percent. The chlorhexidine free base and triclosan may be dissolved in a solvent system comprising water, alcohol, or tetrahydrofuran, and mixtures thereof, to produce an impregnating solution. In one specific, non-limiting example of the invention, a 1:2 ratio of chlorhexidine free base and triclosan may be dissolved in a solvent system which is 70 percent tetrahydrofuran and 30 percent reagent alcohol. A medical article, for example, a polyurethane article, may be impregnated with chlorhexidine free base/triclosan by immersing the article in such an impregnating solution so that the medical article swells without losing substantial structural integrity. After impregnation, the article may be dried, and then optionally coated with a polymeric solution, according to the two-step method set forth above.

Anti-infective medical articles prepared by other methods (e.g., extrusion, casting) but being otherwise substantially the same as articles produced by dipping or soaking, are within the scope of the claimed invention.

5. EXAMPLE

COMBINATIONS OF CHLORHEXIDINE AND TRICLOSAN EXHIBIT SYNERGISTIC ACTIVITY IN BACTERIAL CULTURES

Various concentrations of chlorhexidine diacetate ("CHA") and/or triclosan ("TC") were dispensed in 1.0 ml trypticase soy broth ("TSB") containing 20 percent bovine calf serum ("BCS") and inoculated with $10^7$ colony-forming units ("CFU") of *Staphylococcus aureus*. After one minute, the cultures were diluted with drug-inactivating medium (1:100 dilution in LTSB drug inactivating medium, which is 5% Tween 80, 2% lecithin, 0.6% sodium oleate, 0.5% sodium thiosulfate, 0.1% protease peptone and 0.1% tryptone) and 0.2 ml of the diluted culture was subcultured on a trypticase soy agar plate for the determination of colony counts. The results, shown in Table I, demonstrate the synergistic activity of combinations of chlorhexidine and triclosan. For example, whereas 500 micrograms per milliliter of CHA causes an approximately 17-fold decrease in CFU, and 500 micrograms per milliliter of triclosan causes an approximately 2400-fold decrease, the combination of these agents is associated with zero CFU, an at least $1 \times 10^7$-fold decrease.

TABLE I

| (Anti-infective CFU/ml Agent kill) | Concentration (μg/ml) | (1 minute) |
|---|---|---|
| CHA | 2000 | $2.1 \times 10^3$ |
| CHA | 1000 | $5.0 \times 10^4$ |
| CHA | 500 | $6.0 \times 10^5$ |
| TC | 500 | $4.2 \times 10^3$ |
| TC | 250 | $2.0 \times 10^5$ |
| CHA + TC | 2000 + 500 | 0 |
| CHA + TC | 2000 + 250 | 0 |
| CHA + TC | 1000 + 250 | 0 |
| CHA + TC | 500 + 500 | 0 |
| CONTROL |  | $1.0 \times 10^7$ |

6. EXAMPLE

COMBINATIONS OF CHLORHEXIDINE AND TRICLOSAN ARE MORE EFFECTIVE THAN COMBINATIONS OF CHLORHEXIDINE AND SILVER SULFADIAZINE WHEN APPLIED TO HYDROPHILIC CATHETERS

Polyurethane central venous catheters fabricated Of Tecoflex 93-A polyurethane were dipped in solutions containing 3 percent of a biomedical poly-urethane (Tecoflex 93-A; "PU") and CHA, TC and/or silver sulfadiazine ("AgSD") dissolved in 30 percent ethanol and 70 percent tetrahydrofuran ("THF") (v/v) and air-dried. Bacterial adherence on these catheters was measured as follows. A 2 cm segment of dipped catheter was suspended in 3 ml TSB containing 10 percent BCS and incubated in a water bath shaker at 37° C. The media was changed daily. After 2 days the catheter segments were removed and transferred to fresh media containing $10^6$ CFU/ml of *Staphylococcus aureus* and incubated for 24 hours. The segments were removed, rinsed with saline, and then suspended in LTSB drug-inactivating medium and sonicated for 20 minutes to remove the adherent bacteria. Aliquots from the LTSB extract were then subcultured on trypticase soy agar plates to determine colony counts. The results are presented in Table II, and demonstrate that combinations of CHA and TC are superior in preventing bacterial adherence when compared with CHA alone or in combination with AgSD.

TABLE II

| Bacteria Coating | Adherent (CFU/ml) |
|---|---|
| 3% PU + 2.5% CHA | $5 \times 10^4$ |
| 3% PU + 1.5% CHA + 0.75% AgSD | $2 \times 10^4$ |
| 3% PU + 1.5% CHA + 1% TC | 5 |
| 3% PU + 1.5% CHA + 7.5% AgSD + 1% TC | 40 |

In additional experiments, additional segments of the same type of polyurethane catheters coated with CHA, TC and/or AgSD were tested for the ability to produce zones of inhibition in trypticase soy agar plates seeded with 0.3 ml of $10^6$ CFU of *Staphylococcus aureus, Enterobacter cloacae, Candida albicans*, and *Pseudomonas aeruginosa*. The coated catheter segments were placed vertically on the seeded plates, which were then incubated for 24 hours at 37° C. before the zones of inhibition were measured. The results, shown in Table III, demonstrate the superior effectiveness of mixtures of chlorhexidine and triclosan.

TABLE III

| | Zone of Inhibition (mm) Coating*: | | | |
|---|---|---|---|---|
| Organism | A | B | C | D |
| S. aureus | 14.5 | 15.0 | 13.0 | 16.5 |
| E. cloacae | 9.0 | 12.0 | 7.5 | 3.0 |
| C. albicans | 12.0 | 12.0 | 11.5 | 0 |
| P. aeruginosa | 12.5 | 12.5 | 12.0 | 0 |

*coating A = 3% PU + 2.25% CHA
coating B = 3% PU + 1.75% CHA + 0.5% TC
coating C = 3% PU + 1.75% CHA + 1.5% AgSD
coating D = 3% PU + 0.5% AgSD + 1.75% TC

7. EXAMPLE

HYDROPHILIC CATHETERS COATED WITH HYDROPHOBIC POLYMER COMPRISING CHLORHEXIDINE AND TRICLOSAN HAVE ANTIMICROBIAL ACTIVITY

The antimicrobial effectiveness of polyurethane central venous catheters (fabricated from Tecoflex 93-A polyurethane) coated with chlorhexidine diacetate and either triclosan or silver sulfadiazine in two polymeric coatings of differing water absorption were tested. The polymeric coatings, applied as set forth in Section 6 above, comprised either polyurethane 93A ("PU 93A"), a hydrophilic polyurethane having a water absorption of about 1–2 percent or polyurethane-silicone interpenetrating polymer ("PTUE 205"), a hydrophobic silicone-polyurethane copolymer having a water absorption of only 0.4%. Antibacterial activity was measured by zones of inhibition, using methods as set forth in Section 6, above. The results, as regards antibacterial activity toward *Staphylococcus aureus, Enterobacter cloacae*, and *Candida albicans* at days 1 and 3 of culture, are shown in Tables IV, V, and VI, respectively, and demonstrate that combinations of chlorhexidine diacetate and triclosan were effective when comprised in hydrophilic (PU 93A) as well as hydrophobic (PTUE 205) coatings.

TABLE IV

Antibacterial Activity Against *S. aureus*

| | Zone of Inhibition (mm) | |
|---|---|---|
| Coating | Day 1 | Day 3 |
| 3% PTUE 205 + 1.5% CHA + 1.5% TC | 16.0 | 11.0 |
| 3% PTUE 205 2% CHA + 0.75% AgSD | 14.5 | 11.0 |
| 3% PU 93A + 1.5% CHA + 1.5% TC | 16.0 | 11.5 |
| 3% PU 93A + 2% CHA + 0.75% AgSD | 14.5 | 11.0 |

TABLE V

Antibacterial Activity Against *E. cloacae*

| | Zone of Inhibition (mm) | |
|---|---|---|
| Coating | Day 1 | Day 3 |
| 3% PTUE 205 + 1.5% CHA + 1.5% TC | 12.0 | 6.0 |

TABLE V-continued

Antibacterial Activity Against *E. cloacae*

| | Zone of Inhibition (mm) | |
|---|---|---|
| Coating | Day 1 | Day 3 |
| 3% PTUE 205 + 2% CHA + 0.75% AgSD | 8.5 | 0 |
| 3% PU 93A + 1.5% CHA + 1.5% TC | 11.0 | 7.0 |
| 3% PU 93A + 2% CHA + 0.75% AgSD | 7.0 | 0 |

TABLE VI

Antibacterial Activity Against *C. albicans*

| | Zone of Inhibition (mm) | |
|---|---|---|
| Coating | Day 1 | Day 3 |
| 3% PTUE 205 + 1.5% CHA + 1.5% TC | 11.0 | 7.0 |
| 3% PTUE 205 + 2% CHA + 0.75% AgSD | 12.0 | 9.5 |
| 3% PU 93A + 1.5% CHA + 1.5% TC | 12.5 | 7.0 |
| 3% PU 93A + 2% CHA + 0.75% AgSD | 10.0 | 6.5 |

8. EXAMPLE

HYDROPHOBIC CATHETERS TREATED WITH HYDROPHOBIC POLYMER COMPRISING CHLORHEXIDINE AND TRICLOSAN HAVE ANTIMICROBIAL ACTIVITY

Silicone central venous catheters fabricated from Dow Corning Q7-4765A silicone polymer or Q7-4765B silicone polymer were used to determine the effectiveness of impregnation with hydrophobic polymers comprising chlorhexidine diacetate and triclosan on hydrophobic substrates. The silicone catheters were soaked for about 30 minutes in a solution of 5 percent methanol and 95 percent THF (v/v) comprising (i) 2 percent medical adhesive Silastic Type A and (ii) chlorhexidine diacetate and either triclosan or silver sulfadiazine. The dipped catheters were dried and then dipped in a solution of 5 percent methanol and 95 percent THF (v/v) containing 5 percent Silastic Type A ("SilA"), and dried again. The catheter segments were then tested for the production of zones of inhibition on trypticase soy agar plates inoculated with *S. aureus* or *E. cloacae*. The results are presented in Table VII.

TABLE VII

| | Zone of Inhibition (mm) | |
|---|---|---|
| Treatment | *S. aureus* | *E. cloacae* |
| 2% SilA + 1.5% CHA + 0.5% TC, then 5% SilA | >50 | 21 |
| 2% SilA + 1.5% CHA + 0.5% AgSD, then 5% SilA | 17 | 15 |

9. EXAMPLE

TRICLOSAN EXHIBITS PROLONGED RELEASE FROM POLYMER COATINGS

Silicone central venous catheters fabricated from Dow Corning Q7-4765A silicone polymer or Q7-4765B silicone polymer were treated as set forth in Section 8, above, and then, immediately after drying, were extracted in dichloromethane/methanol/water (50%/25%/25%, v/v) in order to determine the amount of agent contained in the catheter segment tested (i.e., the uptake). To determine the rate of drug release, catheter segments were suspended in saline and incubated at 37° C. for up to seven days; the saline was collected and replaced with fresh saline on the first day and every 48 hours thereafter, and the amount of drug present in the collected saline was measured. The results are presented in Table VIII.

TABLE VIII

| Treatment | Uptake ($\mu$g/cm) | Day 1 | Release ($\mu$g/cm) Day 3 | Day 5 | Day 7 |
|---|---|---|---|---|---|
| 2% SilA + 2% CHA, then 5% SilA | 60 | 28.0 | 4.1 | 3.1 | 2.6 |
| 2% SilA + 2% TC, then 5% SilA | 1168 | 10.0 | 9.5 | 11.1 | 11.4 |

Silicone catheters impregnated with Silastic Type A comprising either 2% triclosan or 2% chlorhexidine diacetate were then tested for the ability to produce zones of inhibition on trypticase soy agar plates inoculated with *S. aureus*, *E. cloacae*, *C. albicans*, or *P. aeruginosa*. The results of these experiments are shown in Table IX, and demonstrate that when higher concentrations of triclosan or chlorhexidine diacetate alone were used, triclosan-treated catheters were found to be equally or more effective than CHA-treated catheters.

TABLE IX

| | Zones of Inhibition (mm) Treatments: | | | |
|---|---|---|---|---|
| | 2% SilA + 2% CHA, then 5% SilA | | 2% SilA + 2% TC, then 5% SilA | |
| Organism | Day 1 | Day 3 | Day 1 | Day 3 |
| *S. aureus* | 17.5 | 16.0 | >50 | >50 |
| *E. cloacae* | 15.0 | 9.0 | 40.0 | 40.0 |
| *C. albicans* | 13.5 | 6.0 | 13.0 | 13.0 |
| *P. aeruginosa* | 13.0 | 0 | 8.5 | 0 |

10. EXAMPLE

UPTAKE OF CHLORHEXIDINE AND TRICLOSAN IN PTFE GRAFTS

Arterial grafts fabricated from polytetrafluoroethylene ("PTFE") were cut into segments and impregnated with Silastic Type A comprising chlorhexidine diacetate or triclosan in 30% methanol/70% THF (v/v), in proportions set forth below. The treated grafts were then extracted with dichloromethane/methanol/water (50%/25%/25%, v/v), and the amounts of solubilized anti-infective agents were determined. Table X shows the uptake of agent by the treated grafts.

TABLE X

| Treatment | Agent Uptake (μg/cm) |
|---|---|
| 2% SilA + 2% CHA | 895 |
| 2% SilA + 2% TC | 2435 |

11. EXAMPLE

ANTIMICROBIAL EFFECTIVENESS OF MEDICAL ARTICLES FABRICATED FROM TEFLON, DACRON OR NATURAL RUBBER LATEX AND IMPREGNATED WITH COMBINATIONS OF CHLORHEXIDINE AND TRICLOSAN

Chlorhexidine diacetate and either triclosan or silver sulfadiazine, in proportions set forth below, were dissolved in 5% methanol/95% THF (v/v). Segments of Dacron grafts, PTFE grafts, and natural rubber latex urinary catheters were then soaked in the resulting solutions for 15 minutes to impregnate the segments with anti-infective agents. This procedure allows the polymer substrates of the devices to incorporate anti-infective agent. The segments were then removed from the soaking solution, dried, rinsed with water, and wiped. The ability of the treated segments to produce zones of inhibition on trypticase soy agar plates inoculated with S. aureus and E. cloacae was then tested. The results, shown in Tables XI–XIII, demonstrate that the combination of chlorhexidine and triclosan produced superior antimicrobial results compared to the combination of chlorhexidine and silver sulfadiazine.

TABLE XI

PTFE Graft

| | Zone of Inhibition (mm) | |
|---|---|---|
| Impregnating Solution | S. aureus | E. cloacae |
| 5% CHA + 0.5% TC | 37.0 | 22.0 |
| 1.5 CHA + 0.75% AgSD | 22.0 | 16.5 |

TABLE XII

Dacron Graft

| | Zone of Inhibition (mm) | |
|---|---|---|
| Impregnating Solution | S. aureus | E. cloacae |
| 5% CHA + 0.5% TC | >40 | 30.0 |
| 1.5 CHA + 0.75% AgSD | 26.0 | 27.0 |

TABLE XIII

Latex Catheter

| | Zone of Inhibition (mm) | |
|---|---|---|
| Impregnating Solution | S. aureus | E. cloacae |
| 5% CHA + 0.5% TC | 26.0 | 20.0 |
| 1.5 CHA + 0.75% AgSD | 18.0 | 12.0 |

12. EXAMPLE

ANTIMICROBIAL EFFECTIVENESS OF SILICONE CATHETERS PREPARED BY A ONE-STEP IMPREGNATION METHOD

Silicone catheters, as used in Example 8, were prepared by a one-step impregnation method as follows. Segments of the silicone catheters were soaked for about 30 minutes in impregnating solutions of 90% THF/10% methanol (v/v) containing 2% Silastic Type A, chlorhexidine, and either silver sulfadiazine or triclosan. The segments were then dried, and tested for their ability to produce zones of inhibition (at one and three days) in trypticase soy agar plates inoculated with S. aureus, E. cloacae, C. albicans, and P. aeruginosa. The results, presented in Table XIV, demonstrate the effectiveness of chlorhexidine and triclosan-impregnated catheters.

TABLE XIV

| | Zones of Inhibition (mm) Treatments: | | | |
|---|---|---|---|---|
| | 2% SilA + 1.5% CHA, + 0.5% TC | | 2% SilA + 1.5% CHA, + 0.5% AgSD | |
| Organism | Day 1 | Day 3 | Day 1 | Day 3 |
| S. aureus | >40 | 39 | 17.5 | 13.5 |
| E. cloacae | 21 | 21 | 15 | 8 |
| C. albicans | 13.5 | 7 | 13.5 | 6 |
| P. aeruginosa | 13.5 | 6.5 | 13 | 0 |

Additional formulations of impregnating solutions were tested for their ability to render the same type of silicone catheter segments anti-infective against C. albicans, the microorganism which appeared to be inhibited only by relatively high amounts of anti-infective agent. The following impregnating solutions comprised chlorhexidine, triclosan and either Silastic Type A, polycaprolactone, or no polymer in a 5% methanol/95%THF solvent. Table XV shows that when both polymer and anti-infective agent were comprised in the impregnating solution, higher anti-infective activity was achieved.

TABLE XV

| Impregnating Solution | Zone of Inhibition (mm) |
|---|---|
| 4% SilA + 5% CHA + 1% TC | 12.0 |
| 1% polycaprolactone + 5% CHA + 1% TC | 12.0 |
| No polymer, 5% CHA + 1% TC | 6.5 |

13. EXAMPLE

DIFFUSION OF ANTI-INFECTIVE AGENTS FROM MEDICAL ARTICLES TREATED WITH IMPREGNATING SOLUTIONS WITH AND WITHOUT POLYMER

The following impregnating solutions, "A" and "B", were used to impregnate segments of Dacron and PTFE grafts. The treated grafts were then rinsed with saline, and the amounts of anti-infective agent incorporated into the grafts were determined, before and after rinsing, by extraction of anti-infective agent with dichloromethane/methanol/water (50%/25%/25%, v/v). The results, set forth in Table XVI, demonstrate that the addition of a polymer to the impregnating solution produces a treated medical article which exhibits greater retention of anti-infective agent.

Solution A: 1% polycaprolactone+0.1% CHA+0.02% TC, in 5% methanol/95% THF (v/v)

Solution B: 0.1% CHA+0.02% TC, in 5% methanol/95% THF (v/v)

TABLE XVI

| | Drug Levels (μg/cm) | | | |
|---|---|---|---|---|
| | Dacron Graft | | PTFE Graft | |
| Solution: | A | B | A | B |
| Solution A | | | | |
| Before rinsing | 392 | 548 | 73 | 90 |
| After rinsing | 353 | 547 | 56 | 88 |
| Solution B | | | | |
| Before Rinsing | 409 | 573 | 50 | 44 |
| After Rinsing | 132 | 553 | 24 | 44 |

14. EXAMPLE

DRUG UPTAKE AND RELEASE BY HYDROPHILIC CATHETERS IMPREGNATED WITH CHLORHEXIDINE OR TRICLOSAN

Polyurethane central venous catheter segments fabricated of Tecoflex 93-A polyurethane were impregnated with solutions "C", "D", "E", "F" and "G" set forth below by soaking the catheter segments for about two minutes followed by drying and rinsing with water. Drug uptake was measured by extracting the impregnated catheter segments with dichloromethane/methanol/water (50%/25%/25% v/v). Drug release was measured over a period of six days by suspending the catheter segments in saline (one 2 cm segment in 2 ml saline), and agitated in a heated water bath at 37° C.; the saline was changed daily and drug release was measured as described above. The results are shown in Table XVII. Polyurethane, as set forth below, is Tecoflex 93-A polyurethane.

Solution C: 3% polyurethane+3% CHA in 30% reagent alcohol/70% THF

Solution D: 3% polyurethane+3% TC in 30% reagent alcohol/70% THF

Solution E: 3% polyurethane+2% CHA+2% TC, in 30% reagent alcohol/70% THF

Solution F: 2% CHA in 95% ethanol Solution G: 3% CHA+1% TC in 95% ethanol

TABLE XVII

| | | Uptake | Drug Release (μg/cm) Day No. | | | | | |
|---|---|---|---|---|---|---|---|---|
| Solution | Drug | (μg/cm) | 1 | 2 | 3 | 4 | 5 | 6 |
| C | CHA | 197 | 78 | 36 | 20 | 2.6 | 0.8 | 0.8 |
| D | TC | 300 | 0.4 | .13 | 0.1 | 0.1 | 0.1 | 0.1 |
| E | CHA | 202 | 66 | 16.8 | 7.0 | 5.0 | 5.0 | 5.0 |
| | TC | 230 | 0.4 | 0.3 | <.1 | <.1 | <.1 | <.1 |
| F | CHA | 254 | 15 | 9.6 | 7.8 | 2.5 | 2.5 | 2.5 |
| G | CHA | 223 | 7.1 | 3.5 | 3.0 | 0.8 | 0.8 | 0.8 |
| | TC | 368 | <.1 | <.1 | <.1 | <.1 | <.1 | <.1 |

15. EXAMPLE

RELEASE OF CHLORHEXIDINE AND TRICLOSAN FROM IMPREGNATED SILICONE CATHETER SEGMENTS

Segments of silicone central venous catheters fabricated from Dow Corning Q7-4765A silicone polymer or Q7-4765B silicone polymer were impregnated with either solution H or I by soaking for 30 minutes, and then the release of drug was measured daily by methods set forth above. The results of these measurements are presented in Table XVIII.

Solution H: 2% SilA+5% CHA in 10% methanol/90% THF (v/v)

Solution I: 2% SilA+5% CHA+2% TC in 10% methanol/90% THF (v/v)

TABLE XVIII

| | | Daily Release (μg/cm) | | | | |
|---|---|---|---|---|---|---|
| Solution | Drug | Day 1 | Day 2 | Day 3 | Day 4 | Day 5 |
| H | CHA | 2.7 | 1.0 | 0.6 | 0.9 | 0.9 |
| I | CHA | 0.8 | 0.9 | 0.6 | 0.8 | 0.8 |
| | TC | 2.6 | 5.6 | 2.3 | 1.5 | 1.5 |

16. METHOD OF RENDERING POLYURETHANE CATHETERS INFECTION-RESISTANT BY IMPREGNATION WITH A SYNERGISTIC COMBINATION OF CHLORHEXIDINE AND TRICLOSAN

A one-step method ("Method 1") and a two-step method ("Method 2") were used to treat polyurethane catheters.

Method 1: An entire polyurethane central venous catheter assembly including the hub, extension line and catheter body may be soaked in an alcoholic solution containing chlorhexidine and triclosan for a specific time period sufficient to impregnate these elements with chlorhexidine and triclosan without altering the integrity of the polyurethane substrate. The following solvent systems and soaking times are suitable. The concentrations of chlorhexidine and triclosan range from 0.5–5%.

TABLE XIX

| | Solvent system | Soaking time |
|---|---|---|
| 95% | ethanol/5% water | 2–30 minutes |
| 100% | reagent alcohol | 2–30 minutes |
| 90% | reagent alcohol/10% water | 5–60 minutes |
| 80% | reagent alcohol/20% water | 5–60 minutes |
| 70% | reagent alcohol/30% water | 10–60 minutes |
| 90% | ethanol/10% water | 5–60 minutes |
| 80% | ethanol/20% water | 5–60 minutes |
| 70% | ethanol/30% water | 10–60 minutes |
| 20% | methanol/10% isopropanol/ 40% reagent alcohol/ 30% water | 10–60 minutes |

Selection of the solvent mixture depends on the type of polyurethane substrate and antimicrobials used for impregnation. After soaking, the catheter is rinsed in water for 24 to 48 hours to allow the catheter to regain its original integrity and size.

Method 2. A catheter impregnated with chlorhexidine and triclosan according to Method 1 is then dipped in 70% THF/30% reagent alcohol/1–3% poly-urethane/1–3% chlorhexidine/1–3% triclosan.

Catheters prepared by Method 1 provide a relatively slow and steady release rate from the luminal surface and outer surface for a prolonged period of time. This pattern of drug release results from the relatively lower ratio of drug to polyurethane matrix (0.015).

Catheters prepared by Method 2 exhibit biphasic drug release. The higher ratio of drug to polyurethane in the outer coating (1.3) permits an initial release of large amounts of drugs (which may inactivate bacteria entering through the skin at the time of insertion) followed by slow and steady release of drug impregnated in the catheter by Method 1. The outer polyurethane coating acts as a barrier and permits the controlled release of drug over a prolonged period of time.

As specific examples, Tecoflex polyurethane catheters were prepared using the following method and then tested for antimicrobial efficacy in their luminal and outer surfaces:

i) catheters were soaked in 2% chlorhexidine dissolved in 100% reagent grade alcohol for 1 hour, rinsed in water, and dried for 24–48 hours ("Catheter C");

ii) catheters were soaked in 2% chlorhexidine+2% triclosan dissolved in 100% reagent grade alcohol for 15 minutes, rinsed in water, and dried for 24–48 hours ("Catheter TC");

iii) catheters were soaked in 2% triclosan in 70% reagent alcohol/30% water for 2 minutes, rinsed in water, and dried for 24–48 hours ("Catheter T");

iv) catheter C (above) was dipped in 3% polyurethane+2% chlorhexidine dissolved in 70% THF/30% reagent alcohol ("Catheter C-C");

v) catheter C (above) was dipped in 3% polyurethane+2% chlorhexidine+0.75% AgSD dissolved in 70% THF/30% reagent alcohol ("Catheter C-A");

vi) catheter T (above) was dipped in 2% chlorhexidine+2% triclosan dissolved in 70% THF/30% reagent alcohol ("Catheter T-R");

vii) catheter TC (above) was dipped in 2% chlorhexidine+2% triclosan dissolved in 70% THF/30% reagent alcohol ("Catheter TC-R"); and viii) catheter TC (above) was dipped in 2% chlorhexidine+0.75% AgSD dissolved in 70% THF/30% reagent alcohol.

Trypticase soy agar plates were seeded with $10^5$ CFU *Staphylococcus aureus*/ml and 0.5 cm segments of catheter were embedded vertically. The plates were then incubated for 24 hours at 37° C. and zones of inhibition were measured. The results are shown in Table XX.

TABLE XX

| Catheter type (mm) | Zone of Inhibition | |
|---|---|---|
| Surface | Lumen | Outer |
| C | 15 | 15 |
| T | 21 | 21 |
| TC | 25 | 25 |
| C-C | 15 | 18 |
| C-A | 15 | 18 |
| T-R | 21 | 25 |
| TC-R | 23 | 26 |
| TC-A | 23 | 26 |

17. METHOD OF RENDERING POLYURETHANE CATHETERS INFECTION-RESISTANT BY IMPREGNATION WITH A SYNERGISTIC COMBINATION OF CHLORHEXIDINE FREE BASE AND TRICLOSAN

It was further discovered that when catheters were coated using insoluble chlorhexidine free base and triclosan, a soluble chlorhexidine/triclosan complex was formed which improved the drug uptake and, therefore, the efficacy of the catheter.

Method 3: Catheters prepared by Method 1 (see Section 16) were dried for 24–72 hours and then their outer surfaces were dipped in a polyurethane solution (1–3% polyurethane dissolved in THF/alcohol). Catheters prepared by this method exhibited a large amount of drug release initially followed by a small but synergistically effective amount of drug release for a prolonged period of time.

Method 4: Followed the same procedure as Method 1, except that insoluble chlorhexidine free base (CHX) was solubilized with triclosan (1 molar CHX:2 molar triclosan ratio), which forms a complex with CHX. After soaking for 5–10 minutes the catheters were dried for 1–3 days and then the outer surface was dipped in either a polyurethane solution alone (1–3% polyurethane) or a solution of polyurethane containing CHX and triclosan (TC).

When relatively soluble chlorhexidine salts such as chlorhexidine acetate (CHA) were used to impregnate catheters, the release was undesirably rapid. We investigated the use of CHX as a substitute for CHA. CHX is not soluble is water or alcohol but, surprisingly, we found that when it was combined in a 1:2 molar ratio with triclosan, an alcohol soluble complex formed.

The uptake of chlorhexidine from a solution containing CHX-TC complex was greater than that obtained from a CHA-TC solution despite a higher CHA concentration in the soaking solution. Due to higher chlorhexidine levels and higher rate of chlorhexidine release from the substrate resulting from impregnation with CHX-TC complex, the infection resistance of the catheters was greater than those containing only CHA.

Method 5: Same as method 4 but the soaking and outer coating solutions also contained soluble chlorhexidine acetate.

As specific examples, the following experiments were performed using Tecoflex catheters:

(1) Catheters were prepared according to Method 3. Specifically, catheters were soaked in 5% CHA+1% TC dissolved in reagent alcohol for 10 minutes, dried for three days, and then the outer surface was dipped in 2.7% Tecoflex polyurethane dissolved in THF/reagent alcohol (70%/30%); the resulting catheters are referred to as type 1, and the polyurethane/THF/reagent alcohol solution is referred to as Solution J.

(2) A second group of catheters was prepared as in (1), but instead of using Solution J for the outer coating, another solution was used: 0.5% CHX+0.5% TC+2.7% polyurethane dissolved in 70%THF/30% reagent alcohol ("Solution K"). The resulting catheters are referred to as type 2.

(3) Catheters were prepared using Method 5. Specifically, catheters were soaked in a solution containing 2% CHX+2% CHA+2% TC dissolved in reagent alcohol for 10 minutes, dried for 3 days and their outer surfaces were dipped in Solution J. The resulting catheters are referred togas type 3.

(4) Catheters were prepared as in (3) but were dipped in Solution K to produce an outer coating. The resulting catheters are referred to as type 4.

(5) Catheters were prepared according to Method 4. Specifically, catheters were soaked for 10 minutes in 3% CHX+3% TC in reagent alcohol, dried for 3 days, and outer surface coated in Solution J. The, resulting catheters are referred to as type 5.

(6) Catheters were prepared as in (5) but outer surface coated with Solution K. The resulting catheters are referred to as type 6.

(7) Catheters were prepared according to Method 3. Specifically, catheters were soaked in a solution containing 5% CHA+1% TC in reagent alcohol for 10 minutes, dried for 3 days and then outer surface coated using Solution J. The resulting catheters are referred to as type 7.

(8) Catheters were prepared as in (7), except were outer surface coated with 2.7% polyurethane+3% CHA in 70% THF/30% reagent alcohol. The resulting catheters are referred to as type 8.

Segments of catheter types 1–8 were placed vertically in inoculated trypticase soy agar plates inoculated with 108 CFU of *Staphylococcus aureus* per plate, and incubated for 24 hours. After measuring the zones of inhibition, the catheters were transferred daily to fresh culture plates (shown in Table XXI).

TABLE XXI

| Catheter type (mm) | Day | Zone of Inhibition |
|---|---|---|
| 1 | 21 | 12.0 |
| 2 | 21 | 13.0 |
| 3 | 21 | 17.0 |
| 4 | 21 | 20.0 |
| 5 | 21 | 20.0 |
| 6 | 21 | 23.0 |
| 7 | 21 | 5.0 |
| 8 | 21 | 9.0 |

The amount of drug uptake per cm/catheter in catheters prepared using various soaking solutions was measured as set forth above.

TABLE XXII

| | Drug Uptake/cm catheter | |
|---|---|---|
| Soaking Solution | Chlorhexidine | Triclosan |
| 5% CHA | 260–310 | — |
| 5% CHA + 2% TC | 280–300 | 450–480 |
| 2% CHX + 2% TC + 2% CHA | 480–520 | 300–370 |
| 3% CHX + 3% TC | 550–660 | 600–700 |

The luminal adherence of bacteria was quantified in catheters impregnated with antimicrobials and then coated with a solution of 2.7 percent Tecoflex 93A and various antimicrobial agents. Bacterial adherence was measured as follows. 12 cm segments of test and control 7Fr catheters were each connected to an individual channel of a peristaltic pump via an extension line, hub, and injection cap. The hubs were inoculated initially and after 24 hours with $10^6$ cfu of *S. aureus* which causes the extension line to become colonized thus acting as a continuous source of bacteria for seeding lumens. The lumens were continuously perfused at a rate of 20 ml/hour with trypticase soy broth (TSB) diluted 1:10 with physiological saline over the course of 7 days. At the end of one week the catheter segments were disconnected and their outer surfaces disinfected with 70% ethanol. Each lumen was flushed with sterile TSB to remove non-adherent bacteria. Each catheter was then cut into 2 cm segments each of which is further divided into 2 mm subsegments and placed in tubes containing 4 ml of antiseptic inactivating broth (LTSB). The tubes were sonicated for 20 minutes at 4° C. to remove bacteria adhering to the lumens. To quantify the adherence, a 0.5 ml aliquot of the LTSB extract was subcultured on trypticase soy agar plates. The results are shown in Table XXIII.

TABLE XXII

| DRUG IN SOAKING SOLUTION (cfu/cm) | DRUG IN OUTER COATING | BACTERIAL ADHERENCE IN LUMEN |
|---|---|---|
| 5% CHA | 3% CHA | $3 \times 10^4$ |
| 5% CHA + 0.5% TC | 2% CHA + 2% TC | $3 \times 10^2$ |
| 2% CHX + 2% CHA + 2% TC | 2% CHA + 2% TC | 0 |
| 3% CHX + 3% TC | 0.5% CHX + 0.5% TC | 0 |
| 0 (control) | 0 | $4 \times 10^6$ |
| 2% CHX + 2% CHA + 2% TC | no outer coating | 5 |

Various publications are cited herein, which are hereby incorporated by reference in their entireties.

We claim:

1. A hydrophilic polymeric medical article which has been impregnated with a treatment solution comprising (i) between about 1 and 10 percent of a hydrophilic polymer; (ii) between 1 and 5 percent of chlorhexidine, wherein the chlorhexidine consists essentially of a mixture of chlorhexidine free base and a chlorhexidine salt; and (iii) between 0.5 and 5 percent of triclosan.

2. The medical article of claim 1 which is fabricated from a hydrophilic polymer selected from the group consisting of natural rubber latex and biomedical polyurethane.

3. The medical article of claim 1 wherein the hydrophilic polymer in the treatment solution is a biomedical polyurethane.

4. The medical article of claim 2 wherein the hydrophilic polymer in the treatment solution is a biomedical polyurethane.

5. A hydrophilic polymeric medical article which has been impregnated with a treatment solution comprising (i) between about 1 and 10 percent of a hydrophobic polymer; (ii) between 1 and 5 percent of chlorhexidine, wherein the chlorhexidine consists essentially of a mixture of chlorhexidine free base and a chlorhexidine salt; and (iii) between 0.5 and 5 percent of triclosan.

6. The medical article of claim 5 which is fabricated from a hydrophilic polymer selected from the group consisting of natural rubber latex and biomedical polyurethane.

7. The medical article of claim 5 wherein the hydrophobic polymer in the treatment solution is a biomedical silicone polymer.

8. The medical article of claim 6 wherein the hydrophobic polymer in the treatment solution is a biomedical silicone polymer.

9. The medical article of claim 5 wherein the hydrophobic polymer in the treatment solution is a silicone-polyurethane copolymer.

10. The medical article of claim 6 wherein the hydrophobic polymer in the treatment solution is a silicone-polyurethane copolymer.

11. A hydrophobic polymeric medical article which has been impregnated with a treatment solution comprising (i) between about 1 and 10 percent of a hydrophobic polymer; between 1 and 5 percent of chlorhexidine, wherein the chlorhexidine consists essentially of a mixture of chlorhexidine free base and a chlorhexidine salt; and (iii) between 0.5 and 5 percent of triclosan.

12. The medical article of claim 11 which is fabricated from a hydrophobic polymer selected from the group consisting of polytetrafluoroethylene, Dacron, polyvinylchloride, biomedical silicone polymer, and silicone polyurethane copolymer.

13. The medical article of claim 11 wherein the hydrophobic polymer in the treatment solution is a biomedical silicone polymer.

14. The medical article of claim 12 wherein the hydrophobic polymer in the treatment solution is a biomedical silicone polymer.

15. The medical article of claim 11 wherein the hydrophobic polymer in the treatment solution is a silicone-polyurethane copolymer.

16. The medical article of claim 12 wherein the hydrophobic polymer in the treatment solution is a silicone-polyurethane copolymer.

17. A hydrophobic polymeric medical article which has been impregnated with a treatment solution comprising (i) between about 1 and 10 percent of a hydrophilic polymer; (ii) between 1 and 5 percent of chlorhexidine, wherein the chlorhexidine consists essentially of a mixture of chlorhexidine free base and a chlorhexidine salt; and (iii) between 0.5 and 5 percent of triclosan.

18. The medical article of claim 17 which is fabricated from a hydrophobic polymer selected from the group consisting of polytetratluoroethylene, Dacron, polyvinylchloride, biomedical silicone polymer, and silicone polyurethane copolymer.

19. The medical article of claim 17 wherein the hydrophilic polymer is a biomedical polyurethane.

20. A method of preparing an infection resistant medical article comprising:
   (i) placing the medical article in an impregnating solution comprising (a) a solvent selected from the group consisting of water, reagent alcohol, tetrahydrofuran, and mixtures thereof; and (b) chlorhexidine and triclosan in a molar ratio of between 1:1 and 1:3, wherein the total weight of chlorhexidine and triclosan is between 1 and 10 percent of the weight of the impregnating solution and wherein the chlorhexidine consists essentially of a mixture of chlorhexidine free base and a chlorhexidine salt;
   (ii) soaking the medical article in the impregnating solution for a period of time sufficient to allow the medical article to swell and to incorporate the chlorhexidine and triclosan;
   (iii) removing the medical article from the impregnating solution; and
   (iv) drying the medical article.

21. The method of claim 20, wherein the solvent in step (1)(a) is a mixture of reagent alcohol and tetrahydrofuran.

22. The method of claim 20, wherein the ratio of chlorhexidine free base and triclosan in step (1)(b) is about 1:2.

23. The method of claim 20, wherein the total weight percent of chlorhexidine free base and triclosan in step (1)(b) is about 2–10.

24. The method of claim 20, which has further been coated with a coating solution comprising a biomedical polymer.

25. The method of claim 24, wherein the biomedical polymer in the coating solution comprises an antimicrobial agent.

26. The method of claim 20 which is fabricated from polyurethane.

27. The method of claim 26 which is a polyurethane catheter.

28. The method of claim 27 in which both the external and internal surfaces of the catheter are brought into contact with the impregnating solution.

29. The method of claim 27 in which only the external surface of the catheter is brought into contact with the impregnating solution.

30. The method of claim 27, in which only the internal surface of the catheter is brought into contact with the impregnating solution.

* * * * *